United States Patent [19]

Solyom et al.

[11] 4,162,195
[45] Jul. 24, 1979

[54] BIOLOGICAL TESTING DEVICE AND METHOD OF MEASURING TOXICITY OF SEWAGE

[75] Inventors: Peter Solyom, Stockholm; Bengt Boman, Akersberga; Håkan Björndal, Norsborg, all of Sweden

[73] Assignee: Aktiebolaget Källe-Regulatorer, Säffle, Sweden

[21] Appl. No.: 846,454

[22] Filed: Oct. 28, 1977

Related U.S. Application Data

[63] Continuation-in-part of Ser. No. 564,552, Apr. 2, 1975, abandoned.

[30] Foreign Application Priority Data

Apr. 4, 1974 [SE] Sweden ................................ 7404556

[51] Int. Cl.² ............................................. G01N 33/18
[52] U.S. Cl. ........................................ 43/310; 210/15; 210/96.1; 435/32
[58] Field of Search ........ 195/127, 139, 143, 103.5 R, 195/103.5 M; 23/230 B; 210/2, 96, 15

[56] References Cited

U.S. PATENT DOCUMENTS 3,557,954  1/1971  Welch ..................................... 210/96
3,731,522  5/1973  Mikesell ................................ 210/96

Primary Examiner—Alvin E. Tanenholtz
Attorney, Agent, or Firm—Kenyon & Kenyon

[57] ABSTRACT

To test sewage for the possible presence of substances which are toxic with respect to sewage biological purification microorganisms, a sample of the sewage is positively provided with a dissolved oxygen content and is then subjected to the action of microorganisms in a biological mass completely submerged in the sample. The volume of the biological mass is controlled to keep it at a constant level. Thereafter the oxygen content of the sample is measured, and if this content is found to be high, it is known that the sample contains toxic substances and that the sewage sample should be treated otherwise than biologically.

10 Claims, 7 Drawing Figures

BIOLOGICAL TESTING DEVICE AND METHOD OF MEASURING TOXICITY OF SEWAGE

BACKGROUND OF THE INVENTION

This application is a continuation-in-part of application Ser. No. 564,552 filed Apr. 2, 1975 now abandoned.

The general principles of sewage treatment are succinctly described by the text SEWAGE TREATMENT, 2nd Edition, published by John Wiley & Sons, Inc., New York 1956, and therefore this text is incorporated by reference into the following.

Briefly outlined, sewage is a relatively dilute aqueous mixture of the numerous kinds of waste from household and industry that it is convenient and economical to carry away by water. A large proportion of the waste matters is organic in nature and is attacked by microorganisms that feed upon dead organic matter. The microorganisms are living things and are dependent upon oxygen for respiration.

Whenever a suitable contact surface is submerged in sewage, at the interface between the sewage and the surface growths of microorganisms develop on the surface in the form of a slime or biological film or biofilm which team with microorganisms which feed on the sewage's organic matter if the sewage contains sufficient oxygen for consumption by the microorganisms.

With the foregoing in mind, sewage treatment plants in general, whether receiving domestic, industrial or municipal sewage, operate as a biological purification plant. In such a plant the sewage is purified by contact with microorganisms which consume the organic matter in the sewage assuming the presence of adequate oxygen for the life of the microorganisms, and because of the volume of sewage which must be handled, extremely large biological beds or masses are required for the treatment. The activated sludge process described in some detail by the referenced text, is often used.

Sewage treatment plants are in widespread use and normally operate satisfactorily so that the treated sewage can be safely discharged into public water bodies.

Unfortunately it sometimes happens that the sewage going to the treatment plant contains chemical substances which are acutely toxic to the microorganisms relied on for purification. Industrial or plant waste water is a form of sewage that is normally treated in an industrial waste treatment plant by biological means, but it is sometimes fed into municipal sewage for treatment by a municipal sewage treatment plant, in either instance a biological treatment process being involved and requiring large biological masses. Industrial waste water is particularly apt to contain substances which at times are acutely toxic to the microorganisms.

If sewage containing acutely poisonous substances is fed into the biological system of a biological treatment plant, it is possible for the microorganisms to be poisoned and rendered inactive. Such a system is large and involves the use of various devices for sewage aeration as required to normally provide the oxygen for the microorganisms. To return the system to operation, requires draining and cleaning and the regeneration of new and living microorganisms before the system can be returned to operation. The time required by this ranges for from two to three weeks and possibly longer, and during shutdown the sewage keeps arriving at the plant, possibly now free from acutely toxic substances and which must be diverted either to storage, or if it can be safely done, treated in an active biological system if the plant has more than one of these systems.

Prior known methods to prove the toxicity of chemical substances are time-consuming and expensive and can substantially be divided into four main groups:

(1) Introduction of toxic substances in normally operating standard purification plants of active sludge type in addition to a subsequent examination of the deteriorated function. For a reliable judgment of the toxicity of a chemical substance (one concentration level) an examination period of about three weeks is required.

(2) Respirometric measurements made on active sludge in the presence of a substance, which can be easily decomposed biologically, and in absence or presence of a toxic chemical substance in different concentrations. The examination takes about one to two weeks.

(3) Culturing representative microorganisms in purification plants in the presence of a toxic chemical substance in different concentrations. This method is also time-consuming.

(4) Determination of the dehydrogenase activity in the presence of a toxic chemical substance in different concentrations. The dehydrogenase activity of the microorganisms is proved by means of TTC. Said determination is a rather complicated procedure.

However, it is obvious that the presence of any acute toxic substance is not discovered by such methods until the microorganisms have already been poisoned. Consequently, if such a substance is present, the purification process must be interrupted and a new culture be generated. This may cause a shutdown for several weeks.

Now it can be seen that a biological testing device which can be installed in a sewage plant laboratory and which can measure the acute toxicity of incoming sewage quickly enough to permit diversion of toxic sewage from the biological system of the plant quickly enough to eliminate a shutdown of the system due to microorganism poisoning, would be a desirable thing to have. Therefore, the device should be capable of continuous operation to measure the toxicity of a small bypassed sampling flow of the incoming sewage.

The present invention was developed with the object of providing a biological testing device having the characteristics indicated above and to provide a new sewage testing technique or process which can be practiced by using such a device. The invention is now being commercially used satisfactorily in the laboratories of various sewage treatment plants. It can also be used to monitor sewage, particularly industrial waste waters, which can safely and lawfully be discharged into public waters known to contain adequate oxygen for the requirements of microorganisms inherently present in such waters, providing the discharge sewage is free from substances toxic to such microorganisms.

Although it is considered preferable to operate this new device continuously, it can be used discontinuously to test one sewage sample after another.

SUMMARY OF THE INVENTION

Basically, this new device comprises an aerator in the form of a small tank into which a sample of the sewage to be tested is flowed, the tank containing an air injection arrangement and the aerator being generally conventional providing it is capable of bringing the sample to almost oxygen saturation, it being recognized that complete saturation in the academic technical sense cannot be attained easily in the case of a working device of practical construction.

The aerated substantially oxygen saturated sample is then transferred to fill a small casing enclosing the sample and containing a submersed biological bed forming a biological mass or biomass completely submersed in the sample and which is maintained substantially at a constant level. For this purpose the bed is formed by providing in the casing two or more interspaced, interfacing and mutually parallel surfaces which are adapted for relative movement in the extending directions of the surfaces. In the commercial form of the device these surfaces are formed by a stack of a multiplicity of rotating disks with non-rotative disks interposed between each two of the rotating disks, the latter being rotated by a power means outside of the casing. Biological films or biofilms or layers of slime, inherently formed by the microorganisms, are cultured on these surfaces, the otherwise constant growth of these biofilms being kept under control by the abrasion between them resulting from the relative movements of the contact surfaces on which the films or slimes are carried. In this way a biomass submersed in the sample in the casing is maintained in the form of a bed having a biological mass or biomass controlled continuously at substantially a constant level or volume. Thickness is controlled by the interspacing of the surfaces and the transverse or radial extent of the biofilms is controlled inherently by the mechanical extents of the surfaces carrying the biofilms. The surfaces form a stack between which the biofilm thickness is constantly maintained so as to overall form a biological mass or biomass of known and fixed dimensions.

In addition to controlling the biological mass volume in the casing of the device, the relative motion involved assures that the sample in the casing is kept distributed and moving throughout the biological mass. It has been found that to provide more assurance in this direction, the contact surfaces can be made to move as by a reciprocating action in directions at right angles to their planes; in the case of the relatively fixed and rotating disk stack the rotating disks can be reciprocated in their axial direction. In each instance as any two of the two surfaces approach each other they abrade and thus adjust and control the thickness of the biofilms on their surfaces, and when they separate, the sample can radially flow between the films, the overall biomass being maintained at a constant level. Another possibility is to make the interfacing surfaces with intermeshing but interspaced flanges which are annular flanges in the case of the disk construction.

Under the conditions described, the life of the microorganisms in the biomass of controlled dimensions inside of the casing, depends on the toxicity of the sewage sample in which the biomass is immersed. If the microorganisms are not poisoned, they consume much or all of the dissolved oxygen in the sample; if the sewage sample contains acutely toxic poisons the microorganisms in the biomass cannot survive and dissolved oxygen is not consumed.

Therefore, the device includes an oxygen measuring unit through which the sample may be flowed from the casing and the biological bed. This unit can be any of the commercial units which provides a suitable readout of the oxygen content. The amount of oxygen consumed in the casing provides a measure of the toxicity of the sewage sample.

This entire biological testing device can be miniaturized into an apparatus that can be installed singly or in multiple in any sewage treatment plant laboratory. The flow through the three components referred to can be continuous. Because the necessary biological mass is formed between the stack of plates providing the relatively moving surfaces, the biological mass can be very small in size while providing for a quick reaction with the sewage sample. This new device provides an accurate readout detecting the presence of toxic substances in the sewage within above five to seven minutes, thus providing adequate time to divert the sewage flow from the sewage plant's biological system before that system can be materially poisoned.

When the new device detects toxic poisons in a sampling flow of bypassed sewage, it does so by the death of the microorganisms in its small biological mass. Because of the small size of the new device, two or more of them can be provided in a small space, so that a deactivated device can be replaced by a standby device. However, due to the very small mass of biological mass used by the device of this invention, that mass can be regenerated or recultured very quickly, only about from five to six hours normally being required in the absence of extraordinary conditions.

It can be seen that with the biological system of this new device the biological activity involved can be a controlled and known factor. As with any testing device, for accurate results the other factors involved should be controlled. For the almost oxygen saturation of the sewage sample, the aerator can be controlled to hold a substantially constant oxygen content in the sample entering the casing of the biological unit. At a temperature of 25° C. and a pressure of 760 mm Hg the oxygen saturation value of water is 8.6 ppm. At from 6.5 ppm upward of oxygen dissolved in water, the term "almost oxygen saturation" is appropriate, and in the practical operation of the device of this invention an oxygen content of 7 ppm is preferred. An aerator of conventional design can maintain this value of oxygen saturation with reasonable accuracy.

With the oxygen content of the sewage held to a known value and with the biological system of known and constantly fixed dimensions and with the flow rate through the aerator and biological system easily known in the case of continuous operation, the accurate and quick readout by the oxygen measuring unit is made positive and reliable as well as rapid.

Although not previously described, in addition to producing good contact between the microorganisms and the sewage or liquid mixture it is also preferable that the organic load of the influent to the biological system [the biochemical oxygen demand ($BOD_7$)] does not vary substantially if it is desired that a change in oxygen consumption can be detected with maximum speed. Therefore, the influent to the present apparatus is most preferably comprised of a mixture of a synthetic sewage of a preset $BOD_7$-value, which value does not vary substantially, and suitably is between 40 and 60 mg/l, and the sample of the sewage to be measured, as disclosed above. Further the volume of the biological system (preferably being $\geq$ 250 cc), the flow rate and the $BOD_7$-value of the synthetic sewage can be chosen in such a way that the dissolved oxygen content in the effluent from the biological system is close to zero in the absence of toxic substances.

The synthetic sewage can be comprised of a substance or a mixture of substances, which can be easily decomposed biologically, and nutrient salts. The synthetic sewage should provide the microorganisms with a carbon source, e.g. carbohydrates or lower alcohols, such as methanol or ethanol, a nitrogen source, e.g. ammonia, and a phosphorus source such as phosphoric acid.

A suitable synthetic sewage has a $BOD_7$ of at least 50 mg/l and has the following composition:

4800 mg casein peptone
3300 mg beef extract
900 mg sodium chloride
120 mg calcium chloride
60 mg magnesium sulfate The components are dissolved in 5 liters of tap water and diluted with tap water to 120 liters.

However, other synthetic sewage components can also be used and the present invention is not limited to the use of any special synthetic sewage composition.

As indicated above the dissolved oxygen content in the liquid mixture after passage of the biological system is almost zero. However, if the liquid mixture is toxic to the microorganisms in said system the microorganisms consume less or no oxygen and the dissolved oxygen content in the outgoing liquid mixture increases.

The rate of increase in the dissolved oxygen content and its magnitude indicate reduced biological activity and suggest that the reason be investigated and the necessary steps taken to stop the toxic discharge.

After a "complete" poisoning of the microorganisms of the biological system, the biological system regenerates itself from the ambient environment through aeration. The regeneration of the biological system takes about 5 to 6 and possibly up to 12 hours and the present device is then ready for reuse.

BRIEF DESCRIPTION OF THE DRAWINGS

The principles of the present invention are illustrated entirely schematically by the accompanying drawings, in which.

DETAILED DESCRIPTION OF THE INVENTION

Figure 1:
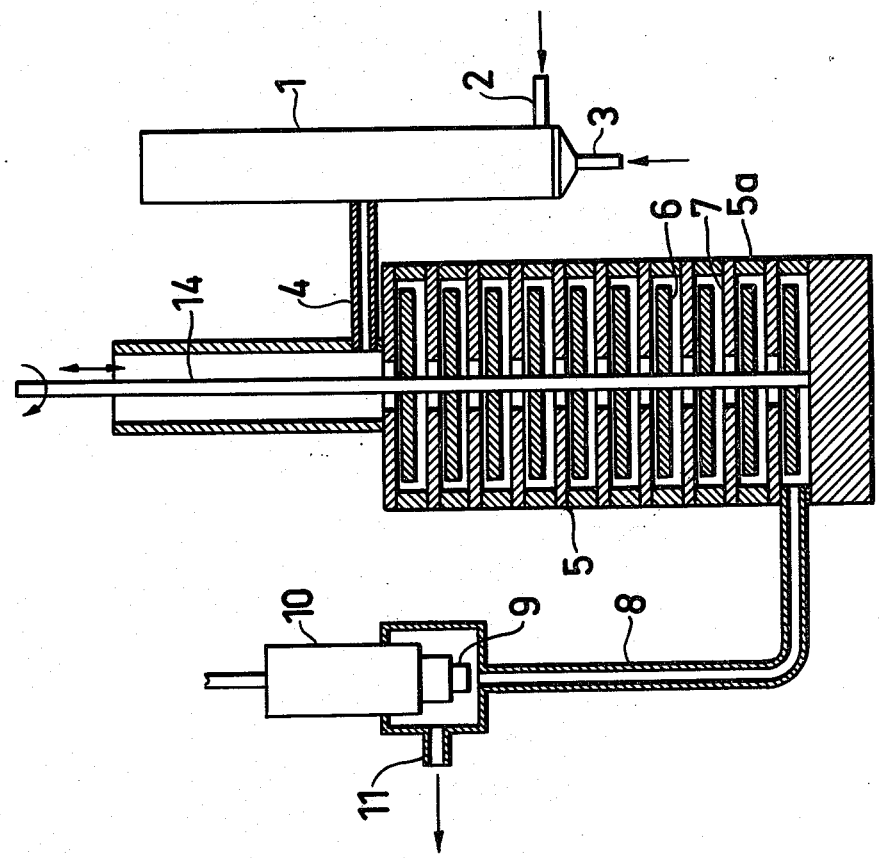
FIG. 1 is a vertical section showing the components of this new biological testing device.

With reference to FIG. 1, a mixture of synthetic sewage and a partial flow of the liquid to be examined is introduced into the preaerator 1 through an inlet 2 and is contacted with air, which is supplied through an inlet 3, the preaerator preferably being dimensioned so that the influent will be almost oxygen saturated as previously described. Then the aerated liquid is passed through a conduit 4 to the biological system 5 consisting of a casing 5a having an inside obviously of known volume and internally containing horizontal rotating circular disks 6 on a vertical shaft 14, and of horizontal stationary inserts 7, which are designed as circular disks and are arranged so that the rotating disks 6 lie between the stationary inserts 7. The casing 5a is completely filled with the sewage sample. The disks 6 and the inserts 7 are preferably parallel, but this is not absolutely necessary and some deviation from a parallel state can be tolerated. By this design a very good contact between the water and the microorganisms of the totally immersed slime layers is obtained. The slime layers are built up both on the rotating and the stationary parts. A particularly good control and constancy of the thickness of the layer is obtained if the shaft 14 is mounted so that a vertical oscillating or reciprocating motion also is produced during the rotation, as previously noted. Since the distance between the rotating plates and the stationary inserts varies, part of the slime layer is periodically abraded by contact between adjacent slime layers.

The liquid flows from the biological system 5 through a conduit 8 to a measuring part consisting of an oxygen electrode 9 and a holder 10 and designed so that the liquid from the biological system passes the membrane of the oxygen electrode at such a high flow rate that the measuring part does not get clogged, continuous measurement of oxygen being made possible. The oxygen content is plotted on a recording means (not shown in FIG. 1).

The liquid flow through the apparatus of the invention is dimensioned on the basis of the respiration of the activated sludge. When using fresh activated sludge an oxygen saturated liquid will be almost entirely free of oxygen in about 5 minutes. Therefore, the detention time in the biological system has been chosen to be 5-6 minutes. With the biological system designed as shown in FIG. 1 this will provide a liquid flow of about 40 ml/min.

The embodiment shown in FIG. 1 may be modified so that the disks 6 are stationary and rotatory inserts 7 are used, or both the disks 6 and the inserts 7 may rotate, suitably in opposite directions, at the same or different speeds.

Figure 2:
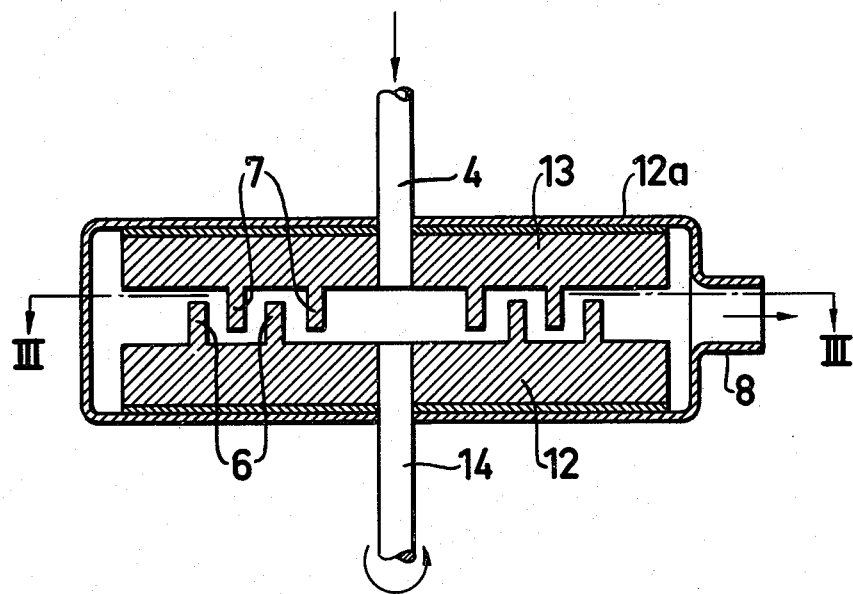
FIG. 2 provides in vertical section an illustration of the use of flanges to form channels throughout the two biofilms which cooperatively form the biological bed of the present invention, in this instance only two oppositely facing interspaced surfaces being illustrated.

An alternative embodiment of the biological system 5 is shown in FIG. 2. This consists of two opposed disks 12, 14, of which at least one is rotating. The disks are provided with flanges 6, 7, the flanges of one disk fitting in the grooves between the flanges of the other disk. In this way a very big contact surface is obtained between the liquid entering through the central portion of the disk 13 and the slime layer formed on the flanges 6, 7, as well as the parts of the disks 12, 13 comprising the surfaces between the flanges. The flanges 6, 7 can have rectangular cross section, a cross section of a truncated cone or some other suitable cross section. The disk 12, 13 are enclosed in a container 12a and the liquid sewage sample which completely fills this container is prevented from circulating through sealings between the walls of the container and the disks. The liquid is passed to the part for measuring oxygen through conduit 8 in the container. The rotating disks may be concentrically or eccentrically mounted on the shaft, and in this way the thickness control of the slime layer is facilitated in the same way as for the embodiment shown in FIG. 1.

Figure 3:
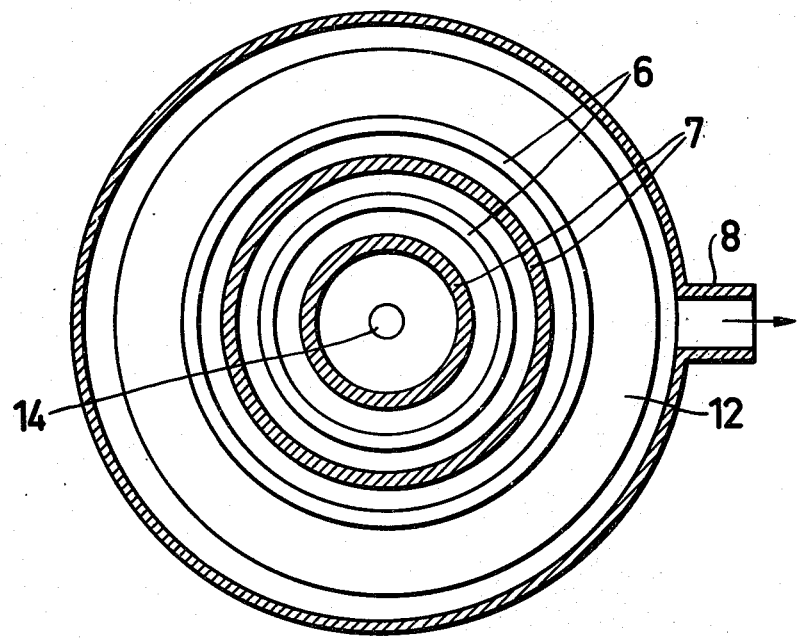
FIG. 3 is a cross section taken on the line III—III in FIG. 2.

FIG. 3 shows in detail in cross section how the flanges 6 on the disk 12 and the flanges 7 on the disk 13 mutually engage each other.

Figure 4:
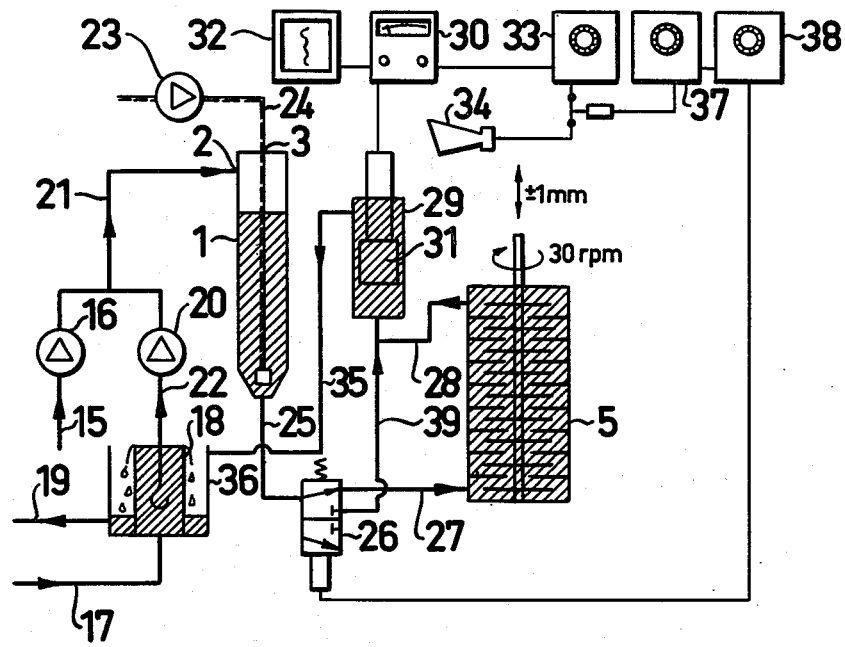
FIG. 4 is a diagram showing the components of the new device as it is commercially made and used.

Referring now to FIG. 4, there is shown a monitoring equipment comprising the biological system 5 designed as described with reference to FIG. 1. An influent of synthetic sewage is pumped through conduit 15 with a pump 16 and mixed in a conduit 21 with the industrial effluent 17 to be monitored, and which is pumped from a tank 18, provided with an overflow outlet 19, through a conduit 22 with a pump 20. The mixed liquid is passed through conduit 21 and introduced in the preaerator 1 through an inlet 2 wherein it is aerated to almost oxygen saturation, air being supplied from a source (not shown) via a pump 23 through a conduit 24 and an inlet 3. From the preaerator 1 the liquid mixture is passed through a conduit 25 and a 3-way valve 26 into the biological system 5 through an inlet conduit 27. The liquid mixture is introduced near the bottom of the biological system 5, passed through the biological system in contact with the slime layers comprising the microorganisms and is withdrawn near the top of the biological system 5 through a conduit 28 and passed to an oxygen measuring means comprising a container 29 for the liquid mixture and a dissolved oxygen content transmitter 30 connected with a dissolved oxygen probe 31 to continuously measure the dissolved oxygen content in the liquid mixture effluent from the biological system 5.

The oxygen content values thus obtained are plotted on a recorder 32 connected with the transmitter 30. Preferably the transmitter 30 is also connected via a high-limit switch 33 to an alarm 34 so as to increase the possibilities to avoid poisoning and disturbances of biological treatment plants. From the container 29 a liquid mixture effluent is withdrawn through conduit 35 and passed into a container 36 which also receives overflow from the container 18. The combined liquids from the container 36 are withdrawn through the overflow outlet 19 for subsequent discharge to the biological treatment plant, possibly after pretreatment if a change in the oxygen consumption has been detected. of the transmitter 30 the system is equipped with an automatic calibration-control unit comprising a timer 37 which activates, at a preset time, a time relay 38 and at the same time it disconnects the alarm function 34. The time relay 38 connects the 3-way valve 26 for a preset adjustable period and the liquid is led outside the biological system 5 directly through a conduit 39 to the probe 31. After about 30 seconds the output signal reaches 7–8 ppm as the oxygen no longer is consumed by the microorganisms. One minute later the time relay 38 disconnects the 3-way valve 26 and the output signal decreases to its original value. After 2.5 minutes from its start (adjustable) the timer 37 connects the alarm system 34 to the high-limit switch 33.

This cycle can be repeated up to once an hour but normally once in 24 hs is sufficient. When the top value of the output signal (preferably recorded) has a tendency to differ by more than 1 ppm from the calibrated value, it is wiser to check the calibration of the dissolved oxygen probe 31.

Figure 5:
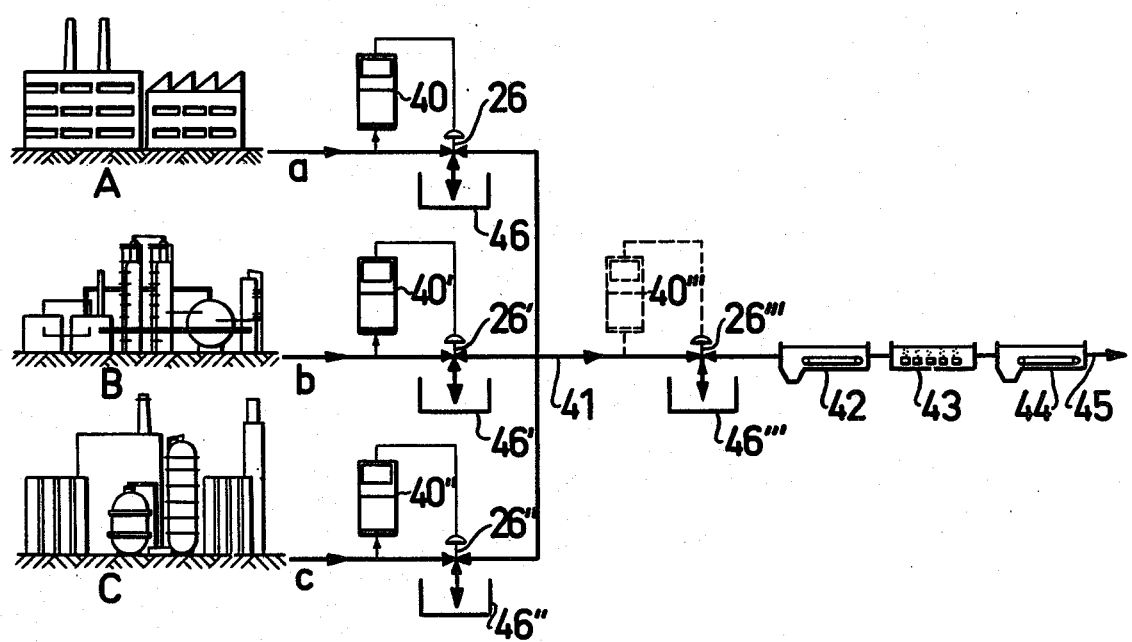
FIG. 5 illustrates the use of the new device in a practical application in the case of industrial plants, the commercial form of the new device providing for a graphical readout of the measurements obtained.

As shown in FIG. 5 the monitor equipment 40 disclosed immediately above may be enclosed in a casing, which casing may be rectangular with a height of about 2 m, a width of about 0.8 m and a depth of about 0.4 m, said casing also encompassing synthetic sewage containers.

A suitable embodiment of the present apparatus is adapted to round-the-clock operation by being equipped with a standby unit comprising a second biological system designed as the biological system 5 shown in FIG. 1 and FIG. 4.

If the microorganisms in the first biological system 5 is poisoned so that it requires time for regeneration the liquid flow to the first biological system 5 is interrupted and instead is directed to the second biological system. Upon regeneration the first biological system then serves as a standby unit.

In FIG. 5 the use of the present apparatus in connection with industrial effluents is illustrated. The effluents a, b and c from three different plants A, B and C are combined to a flow 41 and passed to a conventional biological treatment plant of adequate capacity to handle the combined sewage flow and comprising a primary treatment or settling tank 42, a biological treatment tank 43 and a final clarifier or settling tank 44. The outgoing flow 45 from the tank 44 is passed into a suitable recipient, or if convenient, recycled to the plant for reuse. From each industrial effluent a, b and c a partial or sample flow is bypassed to a monitor equipment 40, 40' and 40", respectively as illustrated in FIG. 4. In case of accidental discharge of toxic substances the effluent in question is passed to a holding tank 46, 46' or 46" for special treatment at a signal by the equipment 40, 40' or 40" to the appropriate one of the 3-way valves 26, 26' or 26".

As an alternative, however less preferred, or in addition to the monitor equipments 40, 40' or 40" a monitor equipment 40''' (shown with dashed lines), a 3-way valve 26''' and a holding tank 46''' may be connected to the combined flow 41 before the flow 41 is introduced into the tank 42 in the purification plant. Preferably the monitor equipment is installed as near the discharge of toxic effluent as possible. Thus suitably the monitor equipment is installed in the industrial plant and connected to the total effluent from the plant or to the effluent from a special division of the plant. In some cases it may be to advantage to install several monitor equipments in one single industrial plant.

As pointed out above the microorganisms comprised in the slime layer consume oxygen when the oxygen containing liquid passes through the biological system, biologically decomposable material in the liquid being decomposed. If the liquid is toxic to the microorganisms, the metabolism of the microorganisms is inhibited and their oxygen consumption stops completely or partly. The measured content of oxygen increases after about 5 minutes, which is equal to the detention time in the biological system, and reaches its maximum concentration after a time depending on the degree of poisoning.

Figure 6:
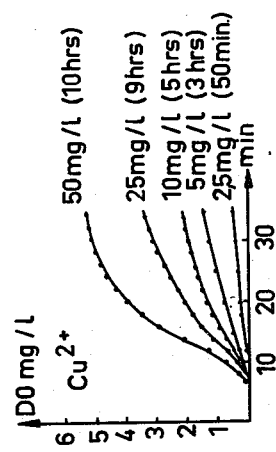
FIGS. 6 and 7 are examples of the graphical results obtained, these indicating the time required for poisoning the microorganisms of the new device's biological system to varying degrees and also indicating within parentheses the times required for regeneration of the device's biological mass or biomass.
Figure 7:
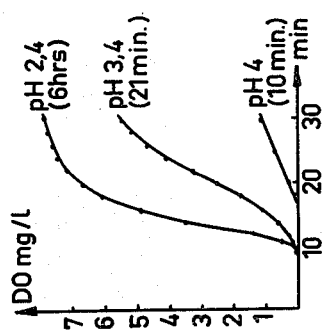

In FIG. 6 the response towards the toxicity of liquids containing copper at different concentrations is shown. In FIGS. 6 and 7 the increasing content of dissolved oxygen (DO) in the effluent from the biological system has been plotted against the time t for the duration of the discharge. The figures in brackets indicate the regeneration time of the biological activity of the biological system without any external intervention.

In FIG. 6 the monitor response towards copper at different concentrations (2.5, 5, 10, 25 and 50 mg/l) shows increasing DO content with increasing concentration. The biological activity is inhibited and the duration of the short-time poisoning varies between 50 minutes and 10 hours. A copper concentration of 1 mg/l did not exhibit any effect. Due to the complexing properties of the synthetic sewage and the absorption of the copper on the biological layer in the system the sensitivity of the monitor is about the same as in a biological treatment plant.

The long-time influence of copper (5 hours) at 2.5, 5 and 10 mg/l give the same monitor response as in the short-term experiment, but the regeneration time increased to about 10 hours, independently of the copper content of the synthetic sewage.

The inhibitory effect of low pH-values is shown in FIG. 7. The monitor response is more dramatic than for copper while the regeneration time is shorter. The system itself acts as a buffer and there is no absorption of hydroxide or hydrogen ions on the biological layer. Even a long-time influence at pH 4 gives a regeneration time of only 3 hours.

As is obvious from FIG. 6 and FIG. 7 the presence of an acute toxic substance in the liquid to be purified can be discovered with the present process and apparatus as early as after about 5-7 minutes and measures can then be taken immediately, e.g. stopping the influent of liquid, or possibly the influent of a partial flow of liquid to the biological purification plant. The rapid response is an additional advantage of the process and the apparatus of the invention, since in this way it is possible to prevent poisoning of the biological stage of the purification plant, which would mean a shutdown of about 2-3 weeks. However, a new microbial culture for the biological system in the present apparatus can be regenerated in about 5-6 hours.

Although schematic, FIG. 1 clearly illustrates how the stack of disks and plates which carry the films forming the biomass, are closely and completely enclosed by the casing 5a. The biological part of the new device is, in effect, a biological filter, the biological mass being of controlled dimensions as previously described. Being schematic, FIG. 1 obviously shows the disk and plates of a much greater thickness than is necessary, the only requirement being that the disks and plates be mechanically stable and rigid enough to support the biofilms substantially rigidly as the films abrade against each other for the control of their thickness. As initially described, the overall biological mass or biomass performs the testing function by the action of the microorganisms, making it clear that the biological mass provides the quickest results when its volume is as large as possible in relationship to the internal volume of the casing 5a. The stacked arrangement of interspaced disks and plates makes it very possible to provide a biomass of great volume as compared to the volume of the sewage flow through the casing of the biological system. The relative rotation or rubbing action provides for a high filtration rate of the sewage being tested, through the biological mass or biological filter.

What is claimed is:

1. A biological testing device for measuring the toxicity of a sewage sample, comprising an aerating means for dissolving oxygen into the sample to form an aerated sample, an enclosure adapted to be completely filled with and completely enclose said aerated sample and containing interspaced interfacing surfaces which are substantially parallel to each other and adapted to support biological films of microorganisms completely submersed in the aerated sample, said surfaces being spaced from each other so as to cause said films to form a biological mass between said surfaces and said surfaces being movable relative to each other in directions causing said films to abrade each other so as to maintain said mass at a thickness substantially fixed by the interspacing distance of the surfaces, means for completely filling said enclosure with said aerated sample, and means for measuring the oxygen content of said sample after a residence time in said enclosure.

2. The device of claim 1 in which said enclosure is formed by a casing, said casing containing a stack of interspaced disks mounted on a rotative shaft which extends through an end of said casing so as to receive rotative force from the casing's outside and with each two of said disks having a non-rotative plate interposed therebetween and interspaced from the two plates, said casing closely and completely enclosing said disks and plates and having an inlet and outlet so that the sewage sample can be flowed through the casing while completely submersing said disks and plates, said disks and plates having mutually interfacing sides forming said surfaces.

3. The device of claim 2 in which said aerator means is for dissolving the oxygen into a continuous flow of the sewage and feeding this flow into the inlet of said casing, and said means for measuring said oxygen content is adapted for continuously measuring the oxygen content in a continuous flow of the sewage and is connected to receive the flow from the outlet of said casing, whereby said device is adapted to continuously test a continuous flow of the sewage sample.

4. The device of claim 2 in which said shaft is axially reciprocative so as to vary the interspacing between said disks and plates.

5. The device of claim 2 in which said surfaces are plain, flat surfaces.

6. The device of claim 2 in which said surfaces have flanges which intermesh and are interspaced.

7. A process for biologically testing a sample of sewage to be purified in a biological bed, comprising aerating said sample so that it is almost completely saturated with oxygen, forming biological films on a plurality of interfacing, interspaced and substantially parallel surfaces and moving said surfaces relative to each other with said films intercontacting so as to abrade one film against the other and control their thickness and form a biological mass of controlled thickness while completely submersing said surfaces and said biological mass in the aerated sample, and thereafter measuring the oxygen content of said sample.

8. A biological testing device for a flow of waste water flowing to a waste water purification plant having a biological stage into which said flow is introduced, said stage containing microorganisms which purify the waste water and which can be poisoned if the waste water contains a substance having acute toxic effect on the microorganisms, said device comprising means for obtaining a partial flow of said waste water before it is introduced into said stage, means for aerating said partial flow so as to dissolve oxygen therein and form a flowing aerated sample of the waste water, an enclosure completely enclosing interspaced interfacing surfaces which are substantially parallel to each other and adapted to support biological films of microorganisms, said surfaces being spaced from each other so as to cause said film to form a biological mass between the surfaces and the surfaces being movable relative to each other in directions causing said films to abrade each other so as to maintain said mass at a thickness substantially fixed by the interspacing distance of the surfaces, means for flowing said flowing sample through said enclosure so as to cause the sample while flowing through the enclosure to completely submerse said biological mass when formed between said surfaces in the enclosure, and measuring means for measuring the oxygen content of said flowing sample while flowing from said enclosure so as to determine whether or not said flowing sample when flowing into said enclosure contained said substance having an acute toxic affect on the microorganisms of said biological mass formed between said surfaces in said enclosure.

9. The device of claim 8 having means for controlling the flow of said waste water to said purification stage of said purification plant and which is operative when said oxygen content measured by said measuring means indicates substantial poisoning of the microorganisms of said biological mass in said enclosure.

10. A process for biologically testing flowing waste water flowing to a waste water purification plant having a biological purification stage into which said flow is introduced, said stage containing microorganisms which can be poisoned if the waste water contains any substance having acute toxic affect on the microorganisms, said process comprising obtaining a partial flow of said waste water before it is introduced into said stage, aerating said partial flow so as to dissolve oxygen therein and form a flowing aerated sample of said waste water, forming biological films on a plurality of interfacing, interspaced and substantially parallel surfaces which are spaced from each other so as to cause the films to form a biological mass between the surfaces, moving said surfaces relative to each other in directions causing said films to abrade each other and maintain said mass at a thickness substantially fixed by the interspacing distance of the surfaces, flowing said flowing aerated sample through said biological mass so that the mass is completely submersed in the sample, measuring the oxygen content of the flowing sample after it flows from said biological mass so as to determine whether or not said flowing sample contains any substance having an acute toxic effect poisoning the microorganisms of said biological mass formed between said surfaces, and at least reducing the flow of said waste water to said purification stage of the plant when said measuring of said oxygen content indicates substantial poisoning of the microorganisms of said biological mass.

* * * * *